(12) United States Patent
Wagner et al.

(10) Patent No.: US 8,852,561 B2
(45) Date of Patent: *Oct. 7, 2014

(54) FLUORIDE VARNISH COMPOSITIONS INCLUDING AN ORGANO PHOSPHORIC ACID ADHESION PROMOTING AGENT

(71) Applicant: Ultradent Products, Inc., South Jordan, UT (US)

(72) Inventors: Jeff A. Wagner, Sandy, UT (US); Andy T. Kawamoto, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,884

(22) Filed: Feb. 7, 2013

(65) Prior Publication Data

US 2013/0149391 A1 Jun. 13, 2013

Related U.S. Application Data

(63) Continuation of application No. 12/339,382, filed on Dec. 19, 2008, now Pat. No. 8,383,163.

(60) Provisional application No. 61/024,379, filed on Jan. 29, 2008, provisional application No. 61/049,643, filed on May 1, 2008.

(51) Int. Cl.
| | | |
|---|---|---|
| *A61K 33/42* | (2006.01) | |
| *A61K 33/30* | (2006.01) | |
| *A61K 33/16* | (2006.01) | |
| *A61K 33/24* | (2006.01) | |
| *A61K 8/21* | (2006.01) | |
| *A61Q 11/00* | (2006.01) | |
| *A61K 47/24* | (2006.01) | |
| *A61K 8/55* | (2006.01) | |

(52) U.S. Cl.
CPC ........... *A61K 47/24* (2013.01); *A61K 33/16* (2013.01); *A61K 8/21* (2013.01); *A61Q 11/00* (2013.01); *A61K 8/55* (2013.01)
USPC ............ 424/57; 424/641; 424/650; 424/653; 424/673; 424/674; 424/675; 424/676; 424/606; 106/35; 433/217.1

(58) Field of Classification Search
None
See application file for complete search history.

(56) References Cited

U.S. PATENT DOCUMENTS

| | | |
|---|---|---|
| 2,798,488 A | 7/1957 | Hall |
| 2,869,543 A | 1/1959 | Ratcliff et al. |
| 3,281,124 A | 10/1966 | Pawlowski et al. |
| 3,326,215 A | 6/1967 | Sarnoff et al. |
| 3,348,546 A | 10/1967 | Roberts et al. |
| 3,548,825 A | 12/1970 | Shaw |
| 3,663,501 A | 5/1972 | Adams et al. |
| 3,685,514 A | 8/1972 | Cheney |
| 3,749,084 A | 7/1973 | Cucchiara |
| 3,767,085 A | 10/1973 | Cannon et al. |
| 3,831,816 A | 8/1974 | Pauliukonis |
| 3,872,864 A | 3/1975 | Allen, Jr. |
| 3,940,362 A | 2/1976 | Overhults |
| 4,003,709 A | 1/1977 | Eaton et al. |
| 4,083,955 A | 4/1978 | Grabenstetter et al. |
| 4,150,012 A * | 4/1979 | Joos ........................... 523/116 |
| 4,159,570 A | 7/1979 | Baskas et al. |
| 4,215,985 A | 8/1980 | Madlener |
| 4,229,813 A | 10/1980 | Lilly et al. |
| 4,235,633 A | 11/1980 | Tomioka et al. |
| 4,243,080 A | 1/1981 | Choksi et al. |
| 4,292,916 A | 10/1981 | Bradley et al. |
| 4,313,440 A | 2/1982 | Ashley |
| 4,374,937 A | 2/1983 | Nemcek et al. |
| 4,391,798 A | 7/1983 | Tavss et al. |
| 4,412,836 A | 11/1983 | Brignola |
| 4,463,875 A | 8/1984 | Tepic |
| 4,464,174 A | 8/1984 | Ennis |
| 4,476,866 A | 10/1984 | Chin |
| 4,480,760 A | 11/1984 | Schonberger |
| 4,515,586 A | 5/1985 | Mendenhall et al. |

(Continued)

FOREIGN PATENT DOCUMENTS

| | | |
|---|---|---|
| CA | 1158063 | 12/1983 |
| DE | 10021313 | 11/2001 |

(Continued)

OTHER PUBLICATIONS

Robert L. Reierson, Regan Crooks, Alvino Gatbaooli and Stewart Warburton. Phosphate Esters: A Natural for Personal Care & Cosmetic Applications. Cosmetic Science Technology, 2006, p. 267.*
U.S. Appl. No. 61/024,379, filed Jan. 29, 2008, Kennard.
U.S. Appl. No. 61/049,643, filed May 1, 2008, Kennard.
"52-11 SureFil High Density Posterior Restorative (project 98-56)", General Dentistry, pp. 1-9, http://www.brooks.af.mil/dis/DIS58/sec5a.htm (Jun. 2, 2005).
"Information for Health Professionals Data Sheet", Atridox, http://www.medsafe.govt.nz/Profs/Datasheet/a/Atridoxgel.htm, Jun. 3, 2005 (7 pages).

(Continued)

*Primary Examiner* — Frederick Krass
*Assistant Examiner* — Michael P Cohen
(74) *Attorney, Agent, or Firm* — Workman Nydegger

(57) ABSTRACT

Fluoride varnish compositions for temporary application and adhesion to a person's teeth. The composition includes a carrier comprising a resin and an adhesion promoting agent comprising an alkyl phosphoric acid. A fluoride ion source (e.g., a fluoride salt such as sodium fluoride) is dispersed within the carrier so as to provide biologically available fluoride ions to the tooth tissue being treated. The composition adheres only temporarily to tooth tissue (e.g., for a period of at least about 4 minutes, but not more than about 1 year), after which the composition spontaneously wears away as a natural result of the action of the tongue, saliva and/or other factors.

29 Claims, 4 Drawing Sheets

(56) References Cited

U.S. PATENT DOCUMENTS

| | | | |
|---|---|---|---|
| 4,657,941 A | 4/1987 | Blackwell et al. | |
| 4,693,706 A | 9/1987 | Ennis, III | |
| 4,743,229 A | 5/1988 | Chu | |
| 4,776,704 A | 10/1988 | Kopunek et al. | |
| 4,966,468 A | 10/1990 | Bruning | |
| 4,987,849 A | 1/1991 | Sherman | |
| 5,000,939 A | 3/1991 | Dring et al. | |
| 5,032,178 A | 7/1991 | Cornell | |
| 5,045,283 A | 9/1991 | Patel | |
| 5,053,339 A | 10/1991 | Patel | |
| 5,057,434 A | 10/1991 | Prusik et al. | |
| 5,228,573 A | 7/1993 | Pavelle et al. | |
| 5,317,987 A | 6/1994 | Muller et al. | |
| 5,328,462 A | 7/1994 | Fischer | |
| 5,354,285 A | 10/1994 | Mazurik et al. | |
| 5,367,002 A * | 11/1994 | Huang et al. | 523/116 |
| 5,380,315 A | 1/1995 | Isono et al. | |
| 5,395,241 A | 3/1995 | Kandelman | |
| 5,395,325 A | 3/1995 | Moreno et al. | |
| 5,425,580 A | 6/1995 | Beller | |
| 5,429,603 A | 7/1995 | Morris | |
| 5,489,267 A | 2/1996 | Moreno et al. | |
| 5,509,530 A | 4/1996 | Wilson | |
| 5,534,562 A | 7/1996 | Jensen et al. | |
| 5,551,778 A | 9/1996 | Hauke et al. | |
| 5,633,836 A | 5/1997 | Langer et al. | |
| 5,643,206 A | 7/1997 | Fischer | |
| 5,665,066 A | 9/1997 | Fischer | |
| 5,697,903 A | 12/1997 | Fischer | |
| 5,725,499 A | 3/1998 | Silverstein et al. | |
| 5,743,886 A | 4/1998 | Lynn et al. | |
| 5,756,356 A | 5/1998 | Yanagi et al. | |
| 5,767,170 A | 6/1998 | Ibsen et al. | |
| 5,779,668 A | 7/1998 | Grabenkort | |
| 5,802,015 A | 9/1998 | Rothschild et al. | |
| 5,839,592 A | 11/1998 | Hayes | |
| 5,876,372 A | 3/1999 | Grabenkort et al. | |
| 5,908,054 A | 6/1999 | Safabash et al. | |
| 5,932,627 A | 8/1999 | Blackwell | |
| 5,957,166 A | 9/1999 | Safabash | |
| 5,981,620 A | 11/1999 | Hammesfahr et al. | |
| 6,071,528 A | 6/2000 | Jensen | |
| 6,089,180 A | 7/2000 | Nichols, Jr. | |
| 6,234,190 B1 | 5/2001 | Fischer et al. | |
| 6,234,196 B1 | 5/2001 | Fischer et al. | |
| 6,309,372 B1 | 10/2001 | Fischer et al. | |
| 6,331,076 B1 | 12/2001 | Coll | |
| 6,458,868 B1 | 10/2002 | Okada et al. | |
| 6,500,879 B1 | 12/2002 | Huang et al. | |
| 6,501,390 B1 | 12/2002 | Chainer et al. | |
| 6,524,559 B2 | 2/2003 | Urai et al. | |
| 6,527,751 B2 | 3/2003 | Fischer et al. | |
| 6,540,072 B1 | 4/2003 | Fischer | |
| 6,575,930 B1 | 6/2003 | Trombley, III et al. | |
| 6,592,251 B2 | 7/2003 | Edwards et al. | |
| 6,612,465 B2 | 9/2003 | Pierson et al. | |
| 6,685,923 B2 | 2/2004 | Peterson et al. | |
| 6,715,645 B2 | 4/2004 | Peuker et al. | |
| 6,743,194 B2 | 6/2004 | Sharon et al. | |
| 6,756,417 B2 | 6/2004 | Allred et al. | |
| 6,759,449 B2 | 7/2004 | Kimura et al. | |
| 6,817,987 B2 | 11/2004 | Vetter et al. | |
| 6,818,682 B2 | 11/2004 | Falsafi et al. | |
| 6,846,300 B2 | 1/2005 | Horth et al. | |
| 6,884,071 B2 | 4/2005 | Martin | |
| 6,921,380 B1 | 7/2005 | Epstein et al. | |
| 7,166,651 B2 | 1/2007 | Qian | |
| 7,168,847 B2 | 1/2007 | Frei et al. | |
| 7,214,726 B2 | 5/2007 | Qian | |
| 7,335,691 B2 | 2/2008 | Orlowski et al. | |
| 7,879,002 B2 | 2/2011 | Jessop | |
| 8,383,163 B2 | 2/2013 | Wagner | |
| 2001/0009931 A1 | 7/2001 | Pflug et al. | |
| 2001/0016703 A1 | 8/2001 | Wironen et al. | |
| 2001/0037091 A1 | 11/2001 | Wironen et al. | |
| 2002/0072714 A1 | 6/2002 | Epstein et al. | |
| 2003/0186196 A1 | 10/2003 | Wang et al. | |
| 2004/0054327 A1 | 3/2004 | Gillespie, III | |
| 2004/0122359 A1 | 6/2004 | Wenz et al. | |
| 2004/0136924 A1 | 7/2004 | Boyd et al. | |
| 2005/0014861 A1 | 1/2005 | Qian | |
| 2005/0023173 A1 | 2/2005 | Paoletti | |
| 2005/0105385 A1 | 5/2005 | McGill et al. | |
| 2005/0281759 A1 | 12/2005 | Tung | |
| 2006/0004120 A1 | 1/2006 | Orlowski et al. | |
| 2006/0171903 A1 | 8/2006 | Yamagishi et al. | |
| 2007/0003493 A1 | 1/2007 | Simonton et al. | |
| 2007/0088097 A1 | 4/2007 | Qian | |
| 2007/0183986 A1 * | 8/2007 | Allred et al. | 424/52 |
| 2007/0203257 A1 | 8/2007 | Qian | |
| 2009/0191279 A1 | 7/2009 | Wagner et al. | |

FOREIGN PATENT DOCUMENTS

| | | | |
|---|---|---|---|
| EP | 661034 | | 12/1994 |
| EP | 1479364 | | 5/2004 |
| FR | WO9926581 | | 6/1999 |
| FR | WO05016170 | | 2/2005 |
| JP | 50049358 | | 5/1975 |
| JP | 1315327 | | 12/1989 |
| JP | 05320032 | | 12/1993 |
| JP | 05320032 | A * | 12/1993 |
| JP | 9182760 | | 7/1997 |
| JP | 2005-104534 | | 4/2005 |
| JP | 2005-186026 | | 7/2005 |
| WO | WO9209870 | | 6/1992 |
| WO | 9965597 | | 12/1999 |
| WO | WO2005050192 | | 6/2005 |
| ZA | 9403163 | | 1/1995 |

OTHER PUBLICATIONS

Seppa, L., et al., "Caries-preventive Effect of fluoride varnish with different fluoride concentrations,"Caries Research, vol. 28(1), pp. 64/67 (Feb. 3, 1993).

Kozykowsky, V., et al., "Histological study of the effect of fluoride preparations for topical use on in vitro treated human enamel surfaces," Deutsche Stematologie, vol. 23(11), pp. 809-816 (Nov. 1973).

Merck Index, online edition, accessed Sep. 15, 2008, NaF.

He et al., "Monolayer formation of Alkyl Chain-Containing Phosphoric Acid Amphiphilies at the Air/Water (pH 5.6) Interface: Influence of Temperature and Cations", Journal of Colloidal and Interface science 246, 335-342 (Feb. 15, 2002).

Shen et al,. "Assessing fluoride concentration uniformity and fluoride release from three varnishes", American Dental Association, vol. 133, Feb. 2002 (Abstract).

Williams, B., et al., "Fissure sealants: a 4-year clinical trial comparing an experimental glass polyalkenoate cement with a bis glycidyl metharcrylate resin used as fissure sealants," Br dent J. Feb. 10, 1996;180(3):104-8 Accession No. 8746143 [PubMed—Indexed for MEDLINE] (Abstract).

Ripa, L., Sealants Revisited: an update of the effectiveness of pir- and-fissure sealants, Caries Res. Dec. 1993;27 Suppl 1:77-82 Accession No. 8500131 [PubMed—Indexed for Medline](abstract).

Irmansyah et al., "In vitro fluoride uptake by bovine enamel during use of cyanoacrylate adhesives containing fluoride compounds," Journal of Materials Science: Materials in Medicine (Jul. 1990), 1(2), 110-13 Accession No. 1990:618156 CAPLUS (Abstract).

Irmansyah et al., "A caries prophylactic study on artificial lesions in bovine tooth enamel coated with cyanoacrylate adhesives containing fluoride compounds," Journal of Materials Science: Materials in Medicine (Jul. 1990), 1(2), 118-22 Accession No. 1990:618158 CAPLUS (Abstract).

Wakasa, K., "Dental use of alkyl cyanoacrylate monomer including fluoride compounds as a coating agent," Journal of Materials Science Letters (Jan. 1992), 11(5), 286-7 Accession No. 1992:158871 CAPLUS (Abstract).

Boyanov, B., et al., "Study of the effect of fluoride on the insulation properties of some alkyl-2-cyanoacrylate preparations for caries-prevention," Problemi na Stomatologiyata (1976) Moscow, 4, 9-15 Accession No. 1978:83415 CAPLUS (Abstract).

(56) References Cited

OTHER PUBLICATIONS

Swartz, et al., "Addition of Fluoride to Pit and Fissure Sealants—a Feasability Study," J. Dent. Res., vol. 55, No. 5, pp. 757-771 (Sep. 1976) (Abstract).
U.S. Appl. No. 11/348,055, Apr. 30, 2008, Office Action.
U.S. Appl. No. 11/537,807, Jun. 23, 2008, Office Action.
U.S. Appl. No. 11/348,055, Sep. 17, 2008, Office Action.
U.S. Appl. No. 11/348,055, Apr. 2, 2009, Office Action.
U.S. Appl. No. 11/348,055, Aug. 31, 2009, Office Action.
U.S. Appl. No. 11/348,055, Feb. 4, 2010, Office Action.
U.S. Appl. No. 12/339,382, Aug. 17, 2012, Office Action.
U.S. Appl. No. 12/339,382, Nov. 15, 2012, Notice of Allowance.
U.S. Appl. No. 11/348,055, Oct. 25, 2013, Office Action.

* cited by examiner

US 8,852,561 B2

FLUORIDE VARNISH COMPOSITIONS INCLUDING AN ORGANO PHOSPHORIC ACID ADHESION PROMOTING AGENT

RELATED APPLICATIONS

This application is a continuation of U.S. patent application Ser. No. 12/339,382, filed Dec. 19, 2008, which claims the benefit of U.S. Provisional Application No. 61/024,379, filed Jan. 29, 2008, and U.S. Provisional Application No. 61/049,643, filed May 1, 2008, the disclosures of which are incorporated in their entirety.

BACKGROUND OF THE INVENTION

1. The Field of the Invention

The present invention generally relates to the field of dentistry, and more particularly to fluoride treatment compositions.

2. The Relevant Technology

In the field of dentistry, a fluoride composition is often applied to a patient's teeth as part of a routine dental cleaning. Fluoride compositions are often applied to children's teeth, although they are sometimes applied to adult teeth also. Application of fluoride has been widely recognized as a method for preventing tooth decay.

According to one method, a fluoride gel composition is dispensed within a dental tray, after which the tray is placed over the patient's teeth. The tray holds the fluoride gel composition adjacent to the patient's teeth, and after a desired amount of time (e.g., a minute or less), the tray is removed and the remaining gel composition is rinsed off the patient's teeth.

Although such fluoride gel compositions provide for fluoride treatment of the teeth, the exposure time of the composition to the patient's teeth is limited (e.g., to 30-60 seconds), which is often all that the patient can endure, as the compositions are typically characterized as having poor taste, discomfort and messiness associated with placing a bulky dental tray filled with a fluoride gel into the patient's mouth. It would be an improvement in the art to provide alternative compositions and methods that would allow for substantially increased exposure times with reduced messiness, and that would not be so invasive and uncomfortable from the patient's standpoint.

SUMMARY OF THE PREFERRED EMBODIMENTS

The present invention is directed to a fluoride varnish composition for temporary application and adhesion to a person's teeth. The composition includes a carrier comprising a resin and an adhesion promoting agent comprising an organo phosphoric acid including at least one alkyl group. A fluoride ion source (e.g., a fluoride salt such as sodium fluoride) is dispersed within the carrier so as to provide available fluoride ions to the tooth tissue being treated. The carrier advantageously allows the composition to temporarily adhere to tooth tissue (e.g., for a period of at least about 4 minutes, but not more than about 1 year, more typically about 5 minutes to about 90 days, more typically about 30 minutes to about 5 days), after which the composition spontaneously wears away as a natural result of the action of the tongue, saliva and/or other factors. Of course, the composition may be removed before it wears away naturally, for example, by brushing.

The carrier phase of the fluoride varnish composition may comprise any non-toxic resin material. Natural resins are particularly preferred. Such natural resins are typically characterized as being sticky which, in combination with the organo phosphoric acid adhesion agent, allows the composition to adhere to hard dental tissue. Examples of natural resins include, but are not limited to, rosins, shellac and/or colophonium. In addition, the carrier may further include one or more solvents (e.g., ethanol). Additional components (e.g., solubilizing agents, sweeteners, and/or flavorants) may also be included in the composition.

The fluoride varnish composition may be formulated so as to advantageously provide a desired aesthetic appearance on the surface of the person's teeth. For example, the varnish may be naturally colorless or substantially clear so as to provide little or no visual contrast between the applied composition and the person's teeth. Such a formulation may be preferred where the patient does not wish to draw attention to their fluoride varnished teeth. Alternatively, a colorant may be included (or one or more of the components may naturally color the composition) so as to provide a visual contrast against tooth tissue when applied. Such contrast may be helpful in allowing a dental practitioner to more easily determine where the fluoride varnish has been applied as well as where it may have worn away after some time.

The adhesion agent comprises an organo phosphoric acid having an alkyl group. The alkyl group includes at least two carbon atoms. Preferred alkyl groups include from 3 to about 30 carbon atoms. Mono-alkyl phosphoric acids are particularly preferred. The alkyl group preferably includes from about 5 to about 30 carbon atoms, more preferably from about 10 to about 25 carbon atoms, and most preferably from about 15 to about 22 carbon atoms. Hexadecyl phosphoric acid (having 16 carbon atoms) and docosyl phosphoric acid (having 22 carbon atoms) are particularly preferred as they have been found to provide excellent adhesion properties to the carrier. Docosyl phosphoric acid is also believed to exhibit anti-microbial and anti-viral properties.

The fluoride varnish composition advantageously remains adhered to the person's teeth for an extended, but temporary, period of time. According to one embodiment, the fluoride varnish composition may advantageously remain adhered to the person's teeth so as to provide fluoride treatment for at least about 30 minutes, preferably for at least about 2 hours. In one embodiment the composition may remain adhered at least about 1, or at least about 2 days. In either case, the composition may preferably be formulated so as to spontaneously wear away after no more than about 5 days. Because such embodiments remain adhered for an extended time (e.g., preferably at least about 30 minutes) but also wears away spontaneously after a relatively short period (e.g., 5 days), the composition provides for an extended treatment time but does not remain adhered on a permanent or semi-permanent basis, which is a distinct advantage over compositions and methods that may provide fluoride treatment for a much shorter time period. Of course, the fact that the composition spontaneously wears away without requiring an active step for removal is also advantageous relative to permanent fluoride varnishes.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

I. Introduction

Figure 1:
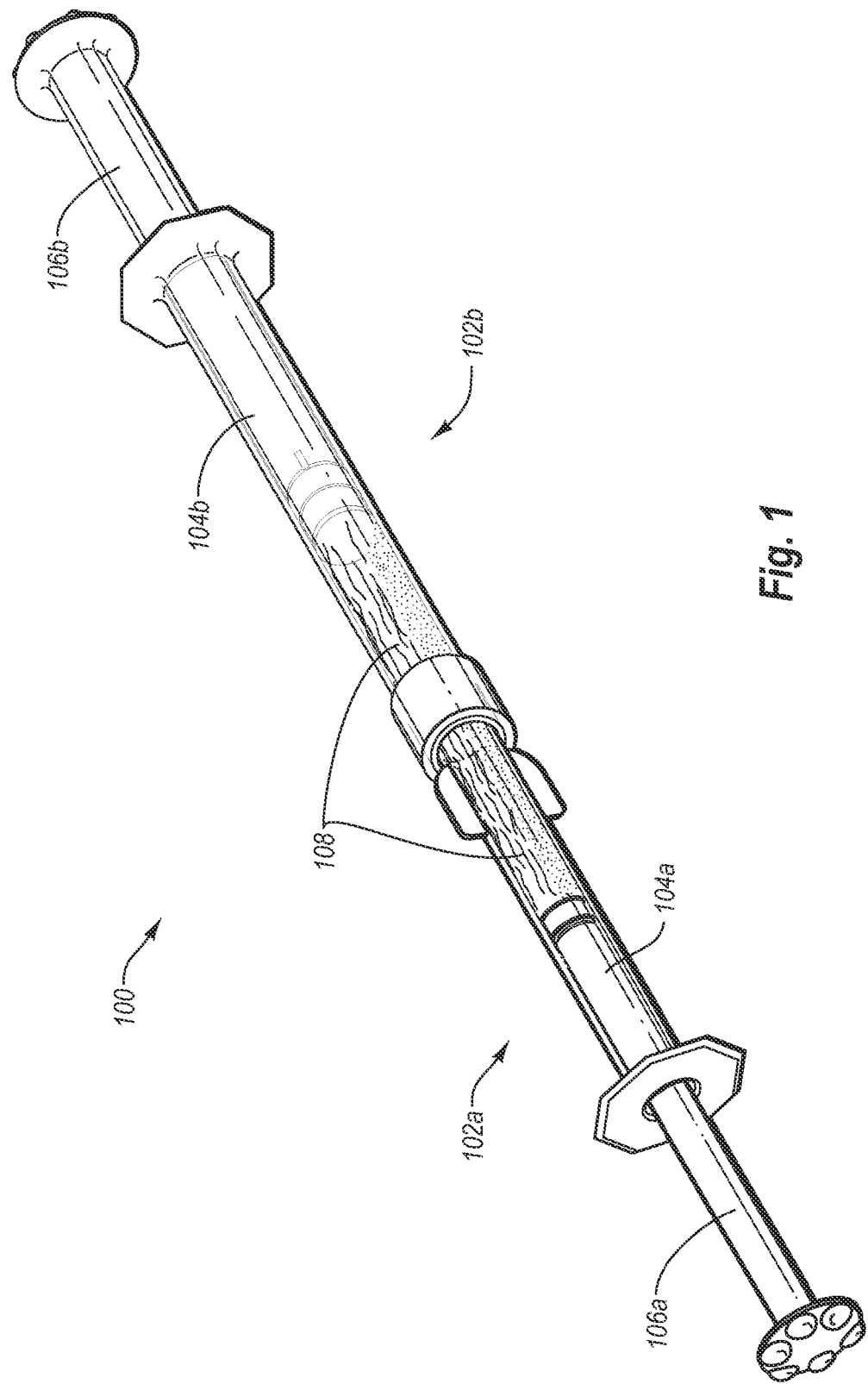
FIG. 1 is a perspective view of an exemplary two-syringe closed vessel mixing system that contains a multi-part fluoride varnish composition.

The present invention is directed to a fluoride varnish composition for temporary application and adhesion to a person's teeth. The composition includes a carrier comprising a resin and an adhesion promoting agent comprising an organo phosphoric acid having at least one alkyl group. Preferably the alkyl group includes between 3 and about 30 carbon atoms. A fluoride ion source (e.g., sodium fluoride) is dispersed within the carrier so as to provide available fluoride ions to the tooth tissue being treated. The carrier advantageously allows the composition to adhere temporarily to tooth tissue (e.g., for a period of at least about 4 minutes, but not more than about 1 year, more typically about 5 minutes to about 90 days, more typically about 30 minutes to about 5 days), after which the composition spontaneously wears away as a natural result of the action of the tongue, saliva and/or other factors. Of course, the composition may be removed earlier than it would wear away naturally, for example, by brushing.

II. Exemplary Fluoride Varnish Compositions

Exemplary fluoride varnish compositions include a fluoride ion source (e.g., a fluoride salt such as sodium fluoride that may be present as a solid phase) dispersed within a sticky, adhesive liquid carrier phase. The liquid carrier includes a resin and at least one alkyl phosphoric acid adhesion agent. Natural resins are preferred. The natural resin may comprise any non-toxic natural resin. Examples of such materials include rosin, colophonium, shellac, and combinations thereof. Commercially available natural resins (e.g., shellac) may be provided with a solvent (e.g., ethanol). One such shellac, known as Refined Pharmaceutical Glaze, is available from Mantrose-Haeuser Co., Inc., located in Westport, Conn. Colophonium is an example of a class of rosins, and specifically refers to a class of sticky, non-synthetic naturally derived sticky resins (e.g., typically derived from various species of pine). Colophonium typically includes a substantial fraction of resin acid components that are isomeric with abietic acid ($C_{20}H_{30}O_2$). Examples of colophonium also may include dihydroabietic acid ($C_{20}H_{32}O_2$) and/or dehydroabietic acid ($C_{20}H_{28}O_2$). Colophonium may range from black to substantially colorless, although it is typically pale yellow to amber in color, and has a density of about 1.07 to about 1.09 g/cm$^3$, and an acid number of not less than about 150. It is typically substantially insoluble in water, and freely soluble in alcohol, benzene, ether, glacial acetic acid, oils, and carbon disulfide. Various materials that are individually referred to as "colophonium" include Canadian balsam, Olibanum balsam, Elemi resin, Opopanax resin, Tolu balsam, Peruvian balsam, and Poly Pale resin, which is a partially dimerized rosin available from Eastman Chemical, located in Kingsport, Tenn.

A particularly preferred rosin material is FORAL AX, a fully hydrogenated tree rosin that has been distilled and dimerized, also available from Eastman Chemical. FORAL AX is nearly colorless, and is substantially more stable than typical rosin and/or colophonium components, resisting oxidation and exhibiting excellent color retention (or more accurately, retention of its substantially colorless characteristics) over time. Another exemplary rosin is STAYBELITE, a partially hydrogenated rosin also available from Eastman Chemical which also exhibits good oxidation resistance and pale color, although FORAL AX is preferred for its better color retention and greater resistance to oxidation.

Synthetic resins may also be suitable for use. An example of such a synthetic resin that may be used is FLUOR PROTECTOR, available from Ivoclar Vivident AG, located in Liechtenstein.

The resin component(s) may preferably be included in the composition in an amount in a range of about 30% to about 80% by weight of the composition, preferably in a range of about 40% to about 70% by weight of the composition, and more preferably in a range of about 45% to about 65% by weight of the composition.

One or more resin components may be combined together with the organo phosphoric acid adhesion promoting agent to form the carrier. Absent the addition of a colorant, any color of the composition is largely determined by the selection of the resin component(s). Many natural resin components naturally have a color to them (e.g., pale yellow). This natural coloring may in some instances be advantageous as it imparts a distinct and visible color contrast to the composition when viewed adjacent the teeth to which the composition is applied. Although advantageous for practical reasons, for aesthetic reasons some patients may prefer a composition that does not provide a visual contrast against the teeth to which the composition is applied. For this reason, the selected resin composition(s) may be substantially colorless (i.e., clear) or of a color (e.g., tooth-colored) so as to blend in with the person's teeth in appearance. FORAL AX is an example of a substantially colorless natural resin. Poly Pale resin and shellac are examples of natural resins exhibiting a pale yellow color.

In a currently preferred embodiment, the adhesion promoting agent comprises an alkyl phosphoric acid (also referred to as an alkyl phosphoric acid ester) having from 3 to about 30 carbon atoms in the alkyl group. Mono-alkyl phosphoric acid esters are particularly preferred, although di-alkyl phosphoric acid components may alternatively and/or additionally be used. The generic chemical structure of one exemplary and currently preferred adhesion agent is as follows:

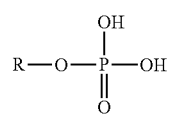

The group "R" represents an alkyl group, preferably having from 3 to about 30 carbon atoms. More preferably the alkyl group includes from about 5 to about 30 carbon atoms, more preferably from about 10 to about 25 carbon atoms, and most preferably from about 15 to about 22 carbon atoms. Hexadecyl phosphoric acid (having 16 carbon atoms) and docosyl phosphoric acid (having 22 carbon atoms) are particularly preferred as they have been found to provide excellent adhesion properties to the carrier. Docosyl phosphoric acid is also believed to exhibit anti-microbial (specifically anti-viral) properties. Structures for both hexadecyl phosphoric acid and docosyl phosphoric acid, respectively, are shown below:

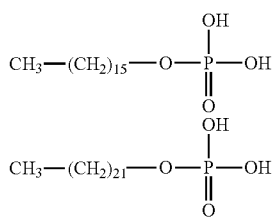

It will be noted that, according to one currently preferred embodiment, the preferred alkyl groups are fully saturated so that they contain no polymerizable groups as the compositions are intended to adhere relatively weakly to the tissue, not to form a permanent bond with underlying tooth tissue. It is believed that the hydrophilic phosphoric acid groups have a strong affinity to the hydrophilic tooth surfaces, which contain high quantities of minerals (e.g., calcium-based minerals). Mono-alkyl phosphoric acids are currently preferred, though di-alkyl phosphoric acids may also be used in some cases. It is believed that because of their relative molecular size (i.e., smaller than a comparable di-alkyl molecule), they are more readily able to temporarily bond to enamel surfaces.

Although adhesion promoting agents having alkyl groups including from 3 to about 30 carbon atoms are currently preferred, it may be possible to employ an adhesion promoting agent having at least one alkyl group that includes significantly more carbon atoms. For example, it may be possible to use alkyl groups up to one thousand, ten thousand, or even 100,000 or more by diluting the adhesion promoting agent with appropriate solvents. When selecting such a material, it would be expected that longer alkyl chains and/or the inclusion of materials including a significant fraction of di-alkyl materials (and thus higher molecular weights for a given alkyl chain length) would require more dilution, all else being equal. That being said, mono-alkyl groups are preferred, and mono-alkyl groups having from 3 to about 30 carbon atoms are particularly preferred for the reasons described above.

The adhesion promoting agent(s) may preferably be included in the composition in an amount from about 1% to about 20% by weight of the composition, more preferably from about 3% to about 10% by weight of the composition, and most preferably from about 5% to about 8% by weight of the composition. The use of higher molecular weight, longer alkyl chain adhesion promoting agents may require relatively lower concentrations, which may even be less than 1% depending on the degree of dilution (e.g., with a solvent) required to form a composition having the desired consistency.

Other components such as solvents, solubilizing agents, sweeteners, and/or flavorants may also be included in preferred embodiments. Ethanol is a particularly preferred solvent as it is non-toxic and generally safe for use in the oral cavity, although other solvents (e.g., acetone or isopropyl alcohol) could alternatively be used. If included, the solvent is typically selected so that it evaporates away after the composition is applied to the teeth. Solvent(s) may preferably be included in the composition in an amount from about 10% to about 60% by weight of the composition, preferably from about 15% to about 45% by weight of the composition, and more preferably from about 20% to about 40% by weight of the composition. The fraction of solvent included depends on the selection of the adhesion promoting agent, as described above.

One or more solubilizing agents such as one or more polyoxyethylene emulsifiers (e.g., polysorbate) may advantageously be included in small amounts to help prevent phase separation of the various carrier components. Exemplary solubilizing agents include various polysorbates (e.g., polysorbate 20, polysorbate 40, polysorbate 60, polysorbate 80), although other similar emulsifiers may also be used. Polysorbate 80, which includes a monooleate type fatty acid associated with the polyoxyethylene sorbitan part of the molecule, is a particularly preferred solubilizing agent. Solubilizing agent(s) may preferably be included in the composition in an amount from about 0.001% to about 3% by weight of the composition, preferably from about 0.01% to about 1% by weight of the composition, and more preferably from about 0.1% to about 0.5% by weight of the composition.

Examples of preferred flavorants include bubble gum, peach, tropical punch, grape, watermelon, lemon-lime, cinnamon, methyl salicylate, natural wintergreen, cool mint, and/or créme de menthe. Examples of preferred sweeteners include sucralose and/or xylitol, although sodium saccharine and/or aspartame could also be used. Sucralose is made by chlorinating sucrose. Xylitol is a sugar alcohol. Sucralose and xylitol are particularly preferred as there is no evidence that either has any carcinogenic effect (as opposed to saccharine). In addition, sucralose and xylitol are particularly preferred over aspartame as the inventors have found that aspartame has less of a sweetening effect, and therefore more aspartame is required to achieve the same perceived sweetness as a lower amount of sucralose or xylitol. Furthermore, xylitol has been found to exhibit antimicrobial effects. Flavorant(s), sweetener(s), and colorant(s) may preferably be included in the composition each in an amount from about 0.1% to about 10% by weight of the composition, preferably from about 0.5% to about 8% by weight of the composition, and more preferably from about 1% to about 5% by weight of the composition.

Depending on the selection of the principal components (e.g., the resin(s), the adhesion promoting agent(s), and any solvent(s)), a rheology modifying agent may also be included. Fumed silica is a preferred optional rheology modifying agent, as it provides handling properties to the varnish composition that are particularly advantageous. The addition of fumed silica has been found to thicken the composition for improved handling, as well as reducing any tendency of a fluoride salt within the composition to settle during storage. One commercially available fumed silica product is AEROSIL 200, available from Degussa. Rheology modifying component(s) may preferably be included in the composition in an amount from about 0.1% to about 10% by weight of the composition, preferably from about 0.5% to about 8% by weight of the composition, and more preferably from about 1% to about 5% by weight of the composition.

Advantageously, the fluoride varnish composition is sufficiently adhesive so as to allow the practitioner to brush or otherwise apply the composition onto a patient's teeth without having to worry about the composition running or dripping off. Exemplary compositions may have a relatively low viscosity (e.g., less than about 1000 centipoise) as compared to fluoride varnish compositions that do not include an adhesion promoting agent. For example, the present compositions may have a viscosity between about 200 centipoise and about 600 centipoise, preferably about 400 centipoise, while typical fluoride varnish compositions not including an adhesion promoting agent have much higher viscosities (e.g., 1000 to 3500 centipoise) to reduce their tendency to run, drip, and slide off the teeth. Although not necessary and perhaps even less preferred, it is of course within the scope of the invention to thicken the composition so as to have a relatively high viscosity (e.g., more than 1000 centipoise).

The fluoride ion source may comprise any suitable fluoride salt, an example of which is sodium fluoride. Other suitable fluoride sources of fluoride ions may include, but are not limited to, $BiF_3$, $SnF_2$, $ZnF_2$, $KF$, $CaF_2$, $ZrF_4$, sodium monofluorophosphate ($Na_2FPO_3$), hexafluorosilicic acid, sodium hexafluorosilicate, or combinations thereof. Sources of fluoride ions which are not technically fluoride salts may also be used. In one example, the fluoride ion source (particularly sodium fluoride) may be included in the composition in an amount from about 0.1% to about 10% by weight of the composition, preferably from about 1% to about 8% by weight of the composition, and more preferably from about 3% to about 7% by weight of the composition.

III. Exemplary Mixing Systems and Methods

FIG. 1 illustrates a syringe-to-syringe mixing system 100 for mixing and dispensing the inventive fluoride varnish composition preparatory to applying it to a person's teeth. Mixing system 100 includes a first syringe 102a coupleable to a second syringe 102b. First syringe 102a includes a first barrel 104a and a first plunger 106a slidably disposed within first barrel 104a. First plunger 106a forms a seal against the inner wall of first barrel 104a, allowing plunger 106a to push the contents of barrel 104a out of the barrel. Second syringe 102b includes a second barrel 104b and a second plunger 106b disposed within second barrel 104b. First syringe 102a and second syringe 102b are illustrated as being coupled together so as to allow the fluoride varnish composition 108 to be cycled back and forth between the syringes so as to substantially suspend the solid fluoride salt phase within the liquid carrier phase of the composition.

Figure 2A:
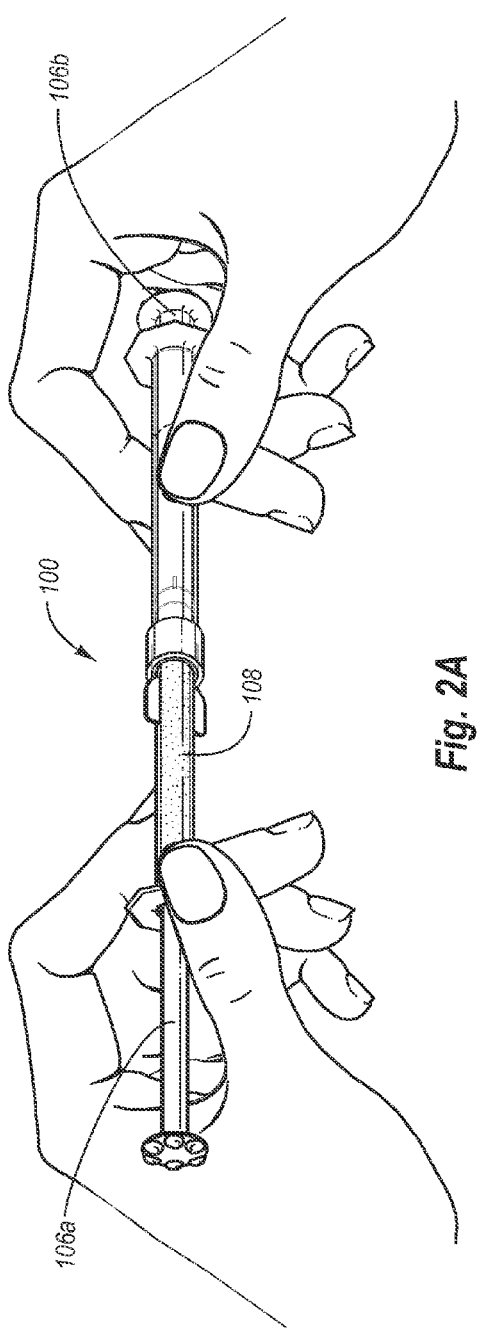
FIGS. 2A-2B depict the exemplary closed vessel mixing system of FIG. 1 being used to cycle the multi-part fluoride varnish composition back and forth.
Figure 2B:
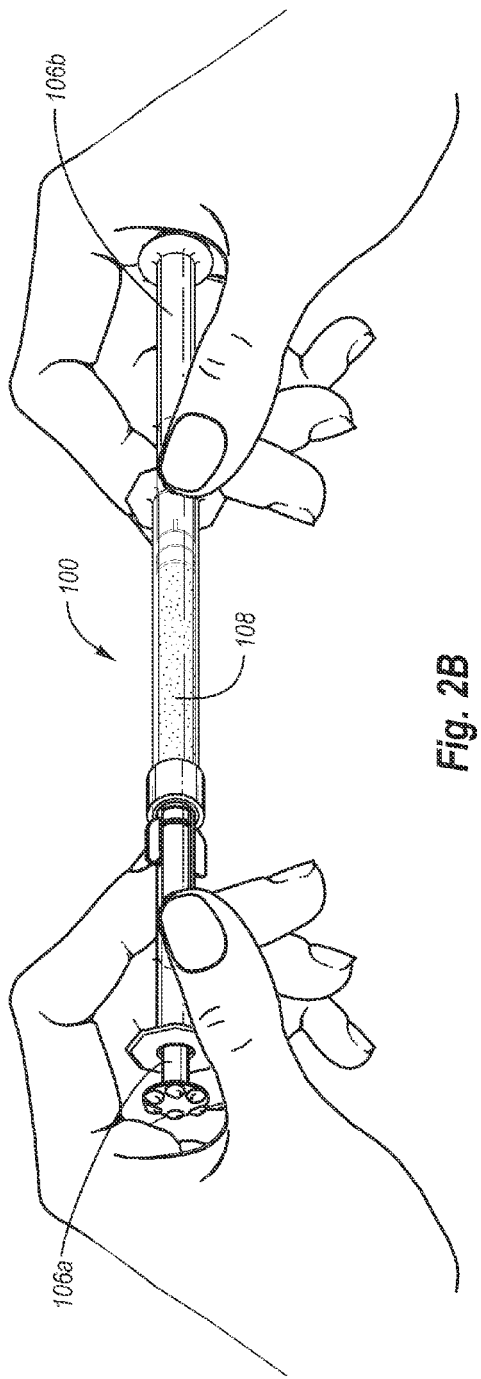

As illustrated in FIGS. 2A and 2B, the dental practitioner is advantageously able to apply turbulence to the multi-phase fluoride varnish composition 108 within first and second syringes of system 100 by manipulating plungers 106a and 106b so as to cycle the fluoride varnish composition 108 back and forth. In such a mixing system the fluoride varnish composition may be cycled back and forth as many times as desired so as to substantially suspend the solid fluoride salt phase within the liquid phase of the composition.

System 100 may advantageously be configured so as to contain a single use quantity of the multi-phase fluoride varnish composition 108. Such a system advantageously provides a single use system that can be provided to the dental practitioner as a uni-dose system which can be mixed and applied to the teeth of a single patient, after which the empty syringe-to-syringe mixing apparatus can be discarded.

Such a syringe-to-syringe configuration is very effective in resuspending the fluoride salt component of the composition within the carrier as the fluoride salt phase may tend to settle out during storage. The inclusion of fumed silica within the composition may reduce any such tendency. In addition, the syringe-to-syringe configuration is very effective in mixing together any other components of the varnish composition which may otherwise tend to form separate phases during prolonged storage. For example, compositions not including a solubilizing agent (e.g., polysorbate 80) to help prevent the resin from separating from the remainder of the carrier may tend to form separate phases during storage. If such is the case with any given varnish composition, the syringe-to-syringe configuration allows for quick and easy remixing of the composition prior to application to a patient's teeth.

Figure 3A:
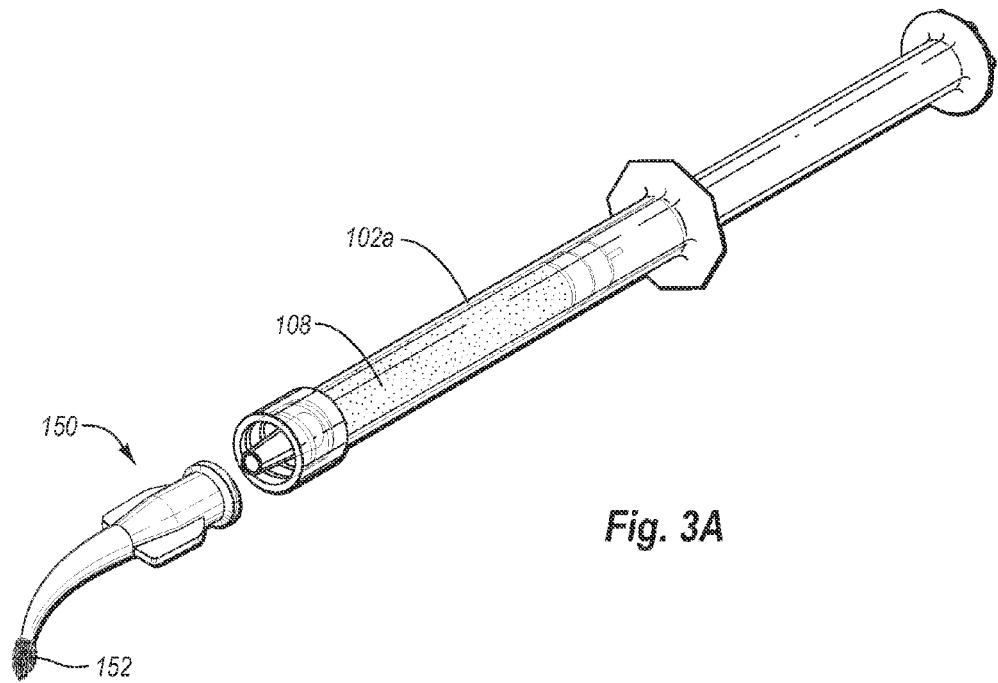
FIGS. 3A-3B illustrate a syringe (e.g., from the mixing system of FIG. 1) being coupled to a flocked applicator tip.
Figure 3B:
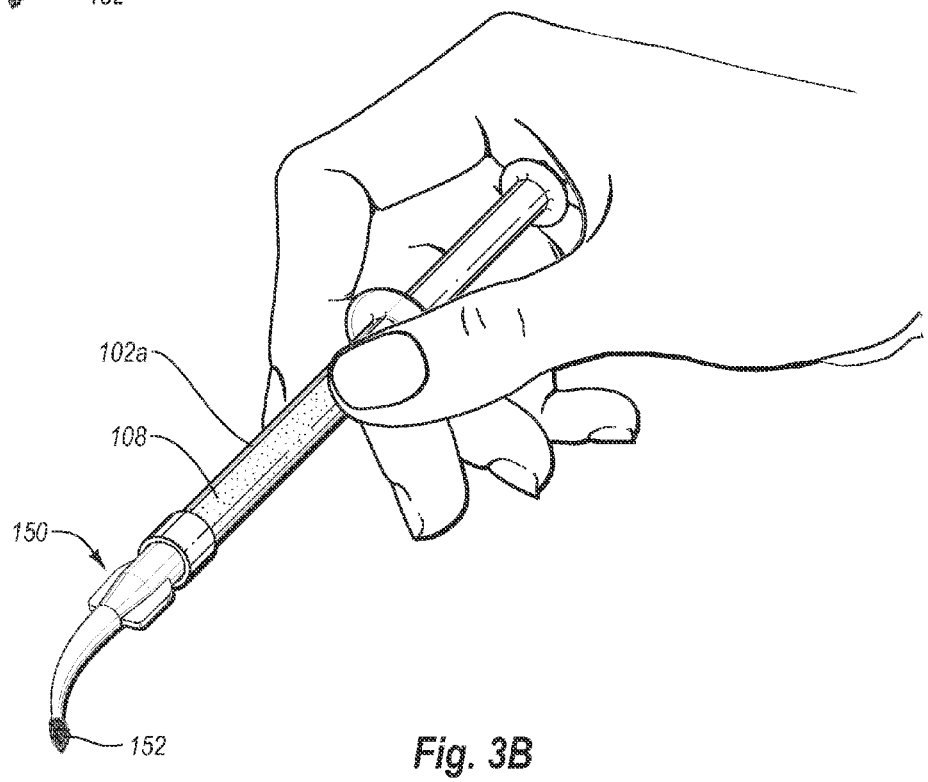

Once the fluoride salt has been substantially suspended, the fluoride varnish composition may then be applied to a person's teeth. According to one method, as seen in FIGS. 3A-3B, an applicator tip 150 may be coupled to syringe 102a containing the fluoride varnish composition 108 after the syringe has been separated from the remainder of the mixing system. Tip 150 may be coupled to first syringe 102a so as to allow the dental practitioner to dispense fluoride varnish composition 108 onto a person's teeth. As illustrated, applicator tip 150 may include a flocked tip 152 so as to allow the user to paint the composition 108 onto the teeth. Use of an applicator tip 150 including a flocked tip 152 may be particularly preferred, although other types of tips (e.g., a tip including a foam pad, a cotton swab, or other absorbent material) may be used. A flocked tip 152 may be particularly preferred as the soft, flexible bristles of a flocked tip allow the composition to be painted onto a tooth surface in a substantially even (i.e., smooth) layer.

Figure 4:
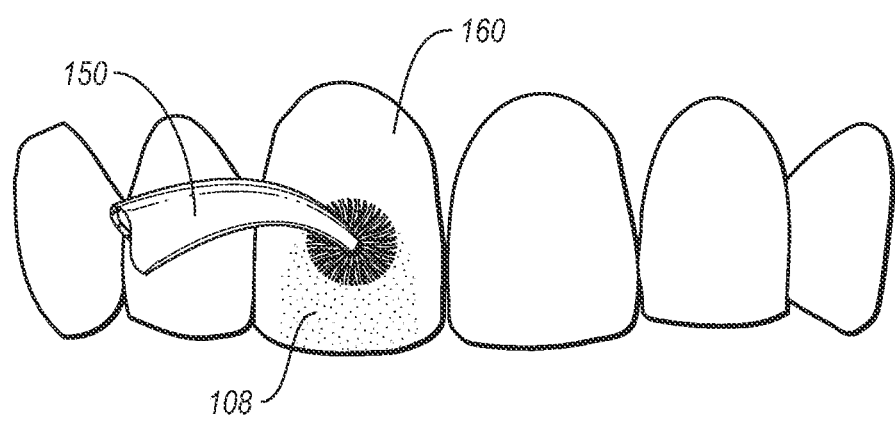
FIG. 4 illustrates the application of a fluoride varnish composition to a tooth using a flocked applicator tip.

FIG. 4 illustrates the dental practitioner using the applicator tip 150 to apply the fluoride varnish composition 108 to a person's tooth 160. The fluoride varnish composition 108 may be substantially colorless or may alternatively provide a visual contrast against the surface of the person's teeth so as to allow a dental practitioner to easily determine where the composition has been applied. Suspension of the fluoride salt phase (and/or remixing of other components) advantageously provides an even distribution of the fluoride salt, carrier, and other components as applied to the teeth, providing a more consistent fluoride concentration and more consistent adhesion characteristics, resulting in overall better treatment across the full surface area of the tooth being treated. Although dispensing and application of the fluoride varnish composition is described in detail using syringe-to syringe mixing device 100, it is to be understood that any apparatus or method of application may be used. Alternative devices that could be used for suspending and dispensing the inventive fluoride varnish composition are disclosed in U.S. patent application Ser. No. 11/348,055 filed Feb. 6, 2006 and entitled METHODS AND SYSTEMS FOR MIXING A MULTI-PART FLUORIDE VARNISH COMPOSITION, and U.S. patent application Ser. No. 12/258,746 filed Oct. 27, 2008 entitled MIXING DEVICE INCLUDING A PLUNGING MIXING MEMBER FOR USE WITH A SYRINGE, each of which is incorporated herein by reference.

The fluoride varnish composition is formulated so as to remain adhered to a person's teeth for an extended period of time relative to current in office fluoride treatments, but to still be temporary. For example, the fluoride varnish may remain adhered for at least about 4 minutes, but no more than about 1 year, more preferably at least about 5 minutes but not more than about 90 days. In currently preferred examples, the fluoride varnish composition may remain adhered to the person's teeth so as to provide fluoride treatment to the teeth for at least about 30 minutes, preferably for at least about 2 hours, more preferably for at least about one day, and most preferably for at least about two days. Such currently preferred examples typically wear away after no more than about 5 days. Of course these stated adhesion times are absent aggressive brushing or other acts calculated to intentionally remove the varnish prior to when it would spontaneously wear away.

Advantageously, substantially all of the composition spontaneously wears away as a natural result of the action of the tongue, saliva and/or other factors within a temporary period, typically no more than about 5 days for currently preferred examples. Of course, the composition may be removed earlier than it would wear away naturally, for example, by aggressive brushing. A small fraction of the composition may remain adhered to the interproximal spaces between the teeth even longer (e.g., as long as 7-10 days for currently preferred examples) absent earlier removal by aggressive brushing and/or flossing.

The composition's extended adherence to tooth tissue is advantageous as the tooth tissues are exposed to fluoride for significantly longer times than is possible with in office fluoride treatments or other treatments in which fluoride exposure is significantly less than the present compositions provide. In particular, extended adherence to the interproximal spaces between the teeth may be particularly advantageous as these locations are often where tooth decay is most likely to occur. Formulating and applying the composition so as to remain adhered for an extended time provides for an extended fluoride treatment time, which is a distinct advantage over compositions that may provide fluoride treatment for a much shorter time period.

IV. EXAMPLES

Example 1

An exemplary hexadecyl phosphoric acid adhesion promoting agent for use in formulating a fluoride varnish composition was produced using the following steps:

1. 77.8 g cetyl alcohol was added to the reactor.
2. A nitrogen purge was applied to the reactor.
3. Cetyl alcohol was heated to 100° C. and stirred until completely melted.
4. The reactor was cooled to 90° C. and 22.2 g phosphorous pentoxide was slowly added so as to ensure the temperature did not exceed 105° C.
5. The mixture was stirred with an electric impeller until $P_2O_5$ has reacted (approximately 1-2 hrs).
6. The solution was filtered using a 300 micron screen and allowed to cool.

The reaction product is believed to have included both mono-hexadecyl phosphoric acid as well as some fraction of di-hexadecyl phosphoric acid. Selection of the reaction temperature as well as the relative fractions of reactants is believed to have influenced the overall product distribution between mono-alkyl components, di-alkyl components, and any other reaction products. For example, maintaining the reaction temperature near 100° C. is believed to favor formation of mono-hexadecyl phosphoric acid (preferable), while increasing the temperature is believed to result in formation of relatively more di-hexadecyl phosphoric acid. Preferably, the amount of cetyl alcohol added to the reactor represents about 70 percent to about 90 percent of the total reactants, while phosphorus pentoxide preferably represents about 10 percent to about 30 percent of the total reactants. Selection of the reactant fractions may also affect product distribution.

Comparative Example

A fluoride varnish composition not including any adhesion promoting agent was formed by mixing together the following components:

| | |
|---|---|
| FORAL AX | 74.11% |
| Ethanol | 12.5% |
| Sodium Fluoride | 5% |
| Cetyl Alcohol | 5.39% |
| Flavorant | 3% |

The fluoride varnish composition was nearly colorless. After application to a patient's teeth, the composition did not adhere well, but tended to slide off the teeth shortly after application.

Example 2

An exemplary fluoride varnish composition was formed using a hexadecyl phosphoric acid adhesion promoting agent produced as in Example 1 by mixing together the following components:

| | |
|---|---|
| Hexadecyl Phosphoric Acid | 5% |
| FORAL AX | 55.9% |
| Ethanol | 30% |
| Polysorbate 80 | 0.1% |
| Sodium Fluoride | 5% |
| Powdered Sucralose | 0.5% |
| Xylitol | 0.5% |
| Flavorant | 3% |

The fluoride varnish composition was nearly colorless. After application to a patient's teeth, the composition remained adhered to the patient's teeth for about two days before spontaneously wearing off. A substantial portion of the composition applied to the interproximal spaces remained adhered even longer.

Example 3

An exemplary fluoride varnish composition was formed using a hexadecyl phosphoric acid adhesion promoting agent produced as in Example 1 by mixing together the following components:

| | |
|---|---|
| Hexadecyl Phosphoric Acid | 5% |
| FORAL AX | 55.9% |
| Ethanol | 29% |
| Polysorbate 80 | 0.1% |
| Sodium Fluoride | 5% |
| Powdered Sucralose | 0.5% |
| Xylitol | 0.5% |
| Flavorant | 4% |

The fluoride varnish composition was nearly colorless. After application to a patient's teeth, the composition remained adhered to the patient's teeth for about two days before spontaneously wearing off. A substantial portion of the composition applied to the interproximal spaces remained adhered even longer.

Example 4

An exemplary fluoride varnish composition was formed using a hexadecyl phosphoric acid adhesion promoting agent produced as in Example 1 by mixing together the following components:

| | |
|---|---|
| Hexadecyl Phosphoric Acid | 5% |
| FORAL AX | 60.9% |
| Ethanol | 24% |
| Polysorbate 80 | 0.1% |
| Sodium Fluoride | 5% |
| Powdered Sucralose | 0.5% |
| Xylitol | 0.5% |
| Flavorant | 4% |

The fluoride varnish composition was nearly colorless. After application to a patient's teeth, the composition remained adhered to the patient's teeth for about two days before spontaneously wearing off. A substantial portion of the composition applied to the interproximal spaces remained adhered even longer.

Example 5

An exemplary fluoride varnish composition was formed using a hexadecyl phosphoric acid adhesion promoting agent produced as in Example 1 by mixing together the following components:

| | |
|---|---|
| Hexadecyl Phosphoric Acid | 5% |
| FORAL AX | 58.4% |
| Ethanol | 26.5% |
| Polysorbate 80 | 0.1% |
| Sodium Fluoride | 5% |
| Powdered Sucralose | 0.5% |
| Xylitol | 0.5% |
| Flavorant | 4% |

The fluoride varnish composition was nearly colorless. After application to a patient's teeth, the composition remained adhered to the patient's teeth for about two days before spontaneously wearing off. A substantial portion of the composition applied to the interproximal spaces remained adhered even longer.

Example 6

An exemplary fluoride varnish composition was formed using a hexadecyl phosphoric acid adhesion promoting agent produced as in Example 1 by mixing together the following components:

| | |
|---|---|
| Hexadecyl Phosphoric Acid | 5% |
| FORAL AX | 45.9% |
| Ethanol | 37% |
| Polysorbate 80 | 0.1% |
| Sodium Fluoride | 5% |
| Powdered Sucralose | 0.5% |
| Xylitol | 0.5% |
| Flavorant | 3% |
| Aerosil 200 (fumed silica) | 3% |

The fluoride varnish composition was nearly colorless. After application to a patient's teeth, the composition remained adhered to the patient's teeth for about two days before spontaneously wearing off. A substantial portion of the composition applied to the interproximal spaces remained adhered even longer.

Example 7

An exemplary fluoride varnish composition was formed using a hexadecyl phosphoric acid adhesion promoting agent produced as in Example 1 by mixing together the following components:

| | |
|---|---|
| Hexadecyl Phosphoric Acid | 20% |
| FORAL AX | 46% |
| Ethanol | 24.9% |
| Polysorbate 80 | 0.1% |
| Sodium Fluoride | 5% |
| Powdered Sucralose | 0.5% |
| Xylitol | 0.5% |
| Flavorant | 3% |

The fluoride varnish composition was nearly colorless. After application to a patient's teeth, the composition remained adhered to the patient's teeth for about two days before spontaneously wearing off. A substantial portion of the composition applied to the interproximal spaces remained adhered even longer.

Example 8

An exemplary fluoride varnish composition is formed using a hexadecyl phosphoric acid adhesion promoting agent produced as in Example 1 by mixing together the following components:

| | |
|---|---|
| Hexadecyl Phosphoric Acid | 3-20% |
| FORAL AX | 45-65% |
| Ethanol | 20-40% |
| Polysorbate 80 | 0.01-0.5% |
| Sodium Fluoride | 4.5-5.5% |
| Aerosil 200 (fumed silica) | 0-5% |
| Powdered Sucralose | 0.5-1% |
| Xylitol | 0.5-1% |
| Flavorant | 2.5-5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 9

An exemplary fluoride varnish composition is formed using a docosyl phosphoric acid adhesion promoting agent by mixing together the following components:

| | |
|---|---|
| Docosyl Phosphoric Acid | 5% |
| FORAL AX | 55% |
| Ethanol | 30% |
| Polysorbate 80 | 0.1% |
| Sodium Fluoride | 5% |
| Aerosil 200 (fumed silica) | 3% |
| Powdered Sucralose | 0.45% |
| Xylitol | 0.45% |
| Flavorant | 1% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 10

An exemplary fluoride varnish composition is formed using a hexadecyl phosphoric acid adhesion promoting agent by mixing together the following components:

| | |
|---|---|
| Hexadecyl Phosphoric Acid | 5% |
| FORAL AX | 65% |
| Ethanol | 25% |
| Sodium Fluoride | 5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 11

An exemplary fluoride varnish composition is formed using a hexadecyl phosphoric acid adhesion promoting agent by mixing together the following components:

| | |
|---|---|
| Hexadecyl Phosphoric Acid | 20% |
| FORAL AX | 60% |
| Ethanol | 15% |
| Sodium Fluoride | 5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 12

An exemplary fluoride varnish composition is formed using a hexadecyl phosphoric acid adhesion promoting agent by mixing together the following components:

| | |
|---|---|
| Hexadecyl Phosphoric Acid | 10% |
| FORAL AX | 55% |
| Ethanol | 30% |
| Sodium Fluoride | 5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 13

An exemplary fluoride varnish composition is formed using a hexadecyl phosphoric acid adhesion promoting agent by mixing together the following components:

| | |
|---|---|
| Hexadecyl Phosphoric Acid | 9.99% |
| FORAL AX | 55% |
| Ethanol | 30% |
| Sodium Fluoride | 5% |
| Polysorbate 80 | 0.01% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 14

An exemplary fluoride varnish composition is formed using a hexadecyl phosphoric acid adhesion promoting agent by mixing together the following components:

| | |
|---|---|
| Hexadecyl Phosphoric Acid | 9.9% |
| FORAL AX | 55% |
| Ethanol | 30% |
| Sodium Fluoride | 5% |
| Polysorbate 80 | 0.1% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 15

An exemplary fluoride varnish composition is formed using a hexadecyl phosphoric acid adhesion promoting agent by mixing together the following components:

| | |
|---|---|
| Hexadecyl Phosphoric Acid | 9.5% |
| FORAL AX | 55% |
| Ethanol | 30% |
| Sodium Fluoride | 5% |
| Polysorbate 80 | 0.5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 16

An exemplary fluoride varnish composition is formed using a hexadecyl phosphoric acid adhesion promoting agent by mixing together the following components:

| | |
|---|---|
| Hexadecyl Phosphoric Acid | 7% |
| FORAL AX | 55% |
| Ethanol | 30% |
| Sodium Fluoride | 5% |
| Aerosil 200 (fumed silica) | 3% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 17

An exemplary fluoride varnish composition is formed using a hexadecyl phosphoric acid adhesion promoting agent by mixing together the following components:

| Hexadecyl Phosphoric Acid | 9.5% |
|---|---|
| FORAL AX | 52.3% |
| Ethanol | 30% |
| Sodium Fluoride | 5% |
| Polysorbate 80 | 0.2% |
| Aerosil 200 (fumed silica) | 3% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 18

An exemplary fluoride varnish composition is formed using a docosyl phosphoric acid adhesion promoting agent by mixing together the following components:

| Docosyl Phosphoric Acid | 5% |
|---|---|
| FORAL AX | 65% |
| Ethanol | 25% |
| Sodium Fluoride | 5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 19

An exemplary fluoride varnish composition is formed using a docosyl phosphoric acid adhesion promoting agent by mixing together the following components:

| Docosyl Phosphoric Acid | 20% |
|---|---|
| FORAL AX | 60% |
| Ethanol | 15% |
| Sodium Fluoride | 5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 20

An exemplary fluoride varnish composition is formed using a docosyl phosphoric acid adhesion promoting agent by mixing together the following components:

| Docosyl Phosphoric Acid | 10% |
|---|---|
| FORAL AX | 55% |
| Ethanol | 30% |
| Sodium Fluoride | 5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 21

An exemplary fluoride varnish composition is formed using a docosyl phosphoric acid adhesion promoting agent by mixing together the following components:

| Docosyl Phosphoric Acid | 9.99% |
|---|---|
| FORAL AX | 55% |
| Ethanol | 30% |
| Sodium Fluoride | 5% |
| Polysorbate 80 | 0.01% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 22

An exemplary fluoride varnish composition is formed using a docosyl phosphoric acid adhesion promoting agent by mixing together the following components:

| Docosyl Phosphoric Acid | 9.9% |
|---|---|
| FORAL AX | 55% |
| Ethanol | 30% |
| Sodium Fluoride | 5% |
| Polysorbate 80 | 0.1% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 23

An exemplary fluoride varnish composition is formed using a docosyl phosphoric acid adhesion promoting agent by mixing together the following components:

| Docosyl Phosphoric Acid | 9.5% |
|---|---|
| FORAL AX | 55% |
| Ethanol | 30% |
| Sodium Fluoride | 5% |
| Polysorbate 80 | 0.5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 24

An exemplary fluoride varnish composition is formed using a docosyl phosphoric acid adhesion promoting agent by mixing together the following components:

| | |
|---|---|
| Docosyl Phosphoric Acid | 7% |
| FORAL AX | 55% |
| Ethanol | 30% |
| Sodium Fluoride | 5% |
| Aerosil 200 (fumed silica) | 3% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 25

An exemplary fluoride varnish composition is formed using a docosyl phosphoric acid adhesion promoting agent by mixing together the following components:

| | |
|---|---|
| Docosyl Phosphoric Acid | 9.5% |
| FORAL AX | 52.3% |
| Ethanol | 30% |
| Sodium Fluoride | 5% |
| Polysorbate 80 | 0.2% |
| Aerosil 200 (fumed silica) | 3% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

Example 26

An exemplary fluoride varnish composition is formed using a docosyl phosphoric acid adhesion promoting agent by mixing together the following components:

| | |
|---|---|
| Docosyl Phosphoric Acid | 3-20% |
| FORAL AX | 45-65% |
| Ethanol | 20-40% |
| Polysorbate 80 | 0.01-0.5% |
| Sodium Fluoride | 4.5-5.5% |
| Aerosil 200 (fumed silica) | 0-5% |
| Powdered Sucralose | 0.5-1% |
| Xylitol | 0.5-1% |
| Flavorant | 2.5-5% |

The fluoride varnish composition is nearly colorless. After application to a patient's teeth, the composition remains adhered to the patient's teeth for about two days before spontaneously wearing off. A substantial portion of the composition applied to the interproximal spaces remains adhered even longer.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A fluoride varnish composition for temporary coating of a tooth surface, comprising:
    a substantially water-insoluble resin;
    an organo phosphoric acid having an alkyl group that contains no polymerizable groups in an amount that promotes adhesion of the varnish composition, including the substantially water-insoluble resin, to tooth surfaces while reducing running or dripping of the varnish composition compared to a composition without the organo phosphoric acid; and
    a fluoride ion source.

2. A fluoride varnish composition as in claim 1, wherein the resin and organo phosphoric acid comprise a sticky, adhesive liquid carrier phase that is formulated to temporarily adhere to tooth surfaces.

3. A fluoride varnish composition as in claim 1, wherein the resin is included in an amount of about 30% to about 80% by weight of the fluoride varnish composition.

4. A fluoride varnish composition as in claim 1, wherein the organo phosphoric acid is included in an amount of about 1% to about 20% by weight of the fluoride varnish composition.

5. A fluoride varnish composition as in claim 1, wherein the varnish composition has a viscosity and consistency so as to facilitate painting of the composition onto tooth surfaces.

6. A fluoride varnish composition as in claim 1, wherein the varnish composition is substantially colorless.

7. A fluoride varnish composition as in claim 1, wherein the varnish composition is formulated so as to remain adhered to tooth surfaces and provide fluoride treatment for at least about 2 hours.

8. A fluoride varnish composition as in claim 1, wherein the varnish composition is formulated so as to remain adhered to tooth surfaces and provide fluoride treatment for at least about 1 day.

9. A fluoride varnish composition as in claim 1, wherein the varnish composition is formulated so as to degrade or spontaneously wear away in less than about 90 days after being placed on a tooth.

10. A fluoride varnish composition as in claim 1, wherein the varnish composition is formulated so as to degrade or spontaneously wear away in less than about 5 days after being placed on a tooth.

11. A fluoride varnish composition as in claim 1, wherein the organo phosphoric acid comprises an alkyl phosphoric acid.

12. A fluoride varnish composition as in claim 11, wherein the alkyl phosphoric acid comprises an alkyl group having from about 3 to about 30 carbon atoms.

13. A fluoride varnish composition as in claim 11, wherein the alkyl phosphoric acid comprises an alkyl group having from about 10 to about 25 carbon atoms.

14. A fluoride varnish composition as in claim 11, wherein the alkyl phosphoric acid comprises an alkyl group having from about 15 to about 22 carbon atoms.

15. A fluoride varnish composition as in claim 11, wherein the alkyl phosphoric acid comprises at least one of hexadecyl phosphoric acid or docosyl phosphoric acid.

16. A fluoride varnish composition as recited in claim 1, wherein the resin comprises a natural resin.

17. A fluoride varnish composition as recited in claim 16, wherein the natural resin comprises at least one of shellac or colophonium.

18. A fluoride varnish composition as in claim 1, further comprising at least one rheology modifying agent.

19. A fluoride varnish composition as in claim 18, wherein the rheology modifying agent comprises fumed silica.

20. A fluoride varnish composition as in claim 1, further comprising at least one of a sweetener or flavorant.

21. A fluoride varnish composition as in claim 1, wherein the fluoride ion source comprises at least one of NaF, $BiF_3$, $SnF_2$, $ZnF_2$, KF, $CaF_2$, $ZrF_4$, sodium mono-fluorophosphate ($Na_2FPO_3$), hexafluorosilicic acid, or sodium hexafluorosilicate.

22. A fluoride varnish composition as in claim 1, wherein the fluoride ion source is included in a range from about 1% to about 8% by weight.

23. A fluoride varnish composition as in claim 1, wherein the varnish composition has a viscosity of less than 1000 centipoise.

24. A fluoride varnish composition as recited in claim 1, wherein the varnish composition has a viscosity from about 200 centipoise to about 600 centipoise.

25. A fluoride varnish composition as in claim 1, further comprising a solvent.

26. A fluoride varnish composition as in claim 1, further comprising a solubilizing agent.

27. A fluoride varnish composition for temporary coating of a tooth surface, comprising:
    an adhesive liquid carrier phase comprising a substantially water-insoluble resin in an amount of about 30% to about 80% by weight and an organo phosphoric acid having an alkyl group that contains no polymerizable groups in an amount of about 1% to about 20%, wherein the sticky, adhesive liquid carrier phase adheres temporarily to tooth tissue; and
    a fluoride ion source dispersed within the adhesive liquid carrier phase,
    wherein the varnish composition has a viscosity and consistency so as to facilitate painting onto tooth surfaces and wherein the organo phosphoric acid improves adhesion of the varnish composition to tooth surfaces.

28. A fluoride varnish composition as in claim 27, further comprising a solubilizing agent.

29. A fluoride varnish composition as in claim 27, further comprising a solvent.

* * * * *